US00PP36098P2

(12) United States Plant Patent
Aguilar Morán

(10) Patent No.: US PP36,098 P2
(45) Date of Patent: Sep. 10, 2024

(54) DESSERT BANANA PLANT NAMED 'WH02'

(50) Latin Name: *M. acuminata*
Varietal Denomination: WH02

(71) Applicant: Fundación Hondureña de Investigación Agrícola (FHIA), San Pedro Sula (HN)

(72) Inventor: Juan Fernando Aguilar Morán, La Lima (HN)

(73) Assignee: Fundación Hondureña de Investigación Agrícola (FHIA) (HN)

( * ) Notice: Subject to any disclaimer, the term of this patent is extended or adjusted under 35 U.S.C. 154(b) by 0 days.

(21) Appl. No.: 18/469,781

(22) Filed: Sep. 19, 2023

(51) Int. Cl.
*A01H 5/08* (2018.01)
*A01H 6/00* (2018.01)

(52) U.S. Cl.
USPC ..... Plt./160

(58) Field of Classification Search
USPC ..... Plt./156, 160
See application file for complete search history.

*Primary Examiner* — Karen M Redden
(74) *Attorney, Agent, or Firm* — Garvey, Smith & Nehrbass, Patent Attorneys, L.L.C.; Seth M. Nehrbass; Fabian M. Nehrbass

(57) ABSTRACT

'WH02' is a hybrid dessert banana variety with a tall stature, is tolerant to Black Sigatoka, and produces high-quality fruit.

6 Drawing Sheets

Latin name of the genus and species of the plant claimed: This triploid plant has only *M. acuminata* in its pedigree and is the product of an inter-specific cross between the triploid (AAA) cultivar 'Williams' and 'Highgate' ('HG'). Its Latin name is *M. acuminata* (AAA) group, representing three genomes of this genus and species.

Variety denomination: 'WH02'.

CROSS-REFERENCE TO RELATED APPLICATIONS

This application is co-pending with the following additional applications by the same inventor: "DESSERT BANANA PLANT NAMED 'SH-4199' (application Ser. No. 18/469,772), "DESSERT BANANA PLANT NAMED 'WW01' (application Ser. No. 18/469,766), "DESSERT BANANA PLANT NAMED 'NW02' (application Ser. No. 18/469,776) and "DESSERT BANANA PLANT NAMED 'HG07' (application Ser. No. 18/469,787). The plants of these applications, as well as the plant of the present application, were created in the banana breeding program of Applicant/Owner/Assignee, FHIA.

STATEMENT REGARDING FEDERALLY SPONSORED RESEARCH OR DEVELOPMENT

Not applicable.

BACKGROUND OF THE INVENTION

1. Field of the Invention

This invention relates to a new and distinctive hybrid banana variety named 'WH02'. This new hybrid variety was the result of a field cross performed in 2016 in La Lima Cortés, Honduras, between 'Williams' x 'Highgate' ('HG') (Both unpatented). 'HG' is a triploid plant (AAA) susceptible to Black Sigatoka leaf spot disease (*Mycosphaerella fijiensis*) and *Fusarium oxysporum* race 1, belonging to the Gros Michel group. 'Williams' is a medium-sized triploid plant (AAA) susceptible to Black Sigatoka leaf spot disease and resistant to *Fusarium Oxysporum* race 1 but susceptible to race 4, belonging to the Cavendish group. 'Williams' is one of the most commercialized bananas worldwide; people prefer it for its flavor, aroma, and size. Both banana varieties were selected from a germplasm collection.

'WH02' is a triploid hybrid (AAA) created for the genetic improvement of the Gros Michel banana group. This hybrid was selected in 2018 from several first-generation seedlings from the cross between 'Williams' x 'HG'. It was chosen as a triploid hybrid, maintaining characteristics of its parent's lines and producing bunches of 18 kilograms. 'WH02'was asexually reproduced by corms by the breeder in La Lima Cortes, Honduras. All plants and fruit run true to the initially selected plant and are identical in all aspects.

The 'WH02' hybrid shares many characteristics with its parent plants, 'Williams', and 'Highgate'. It has a similar leaf shape, plant height, and stem shape. However, the bunch shape is quite different from its parents, and the flavor is slightly altered as well. While 'Williams' and 'Highgate' are both sweet and have a pleasant flavor, the 'WHO2' hybrid is slightly sweeter with a unique taste. Unfortunately, like its parents, it is highly susceptible to black Sigatoka (*Mycosphaerella fijiensis*), a disease that affects banana plants. It's important to note that this comparison is made in the context of commercial varieties, as 'Williams' is one of the most widely commercialized banana varieties in the world and, a parent of this hybrid.

BRIEF SUMMARY OF THE INVENTION

'WH02' is a hybrid dessert banana variety with a tall stature, is tolerant to Black Sigatoka, and produces high-quality fruit.

BRIEF DESCRIPTION OF THE PHOTOGRAPHS

The figures describe the characteristics of the 'WH02' hybrid banana variety at 10.5 months old. The color shown in the photographs is as nearly accurate as reasonably possible in this type's color representation.

FIG. 1 shows the typical appearance of a plant;

FIG. 2A-B shows blotches at the petiole base (A) and a petiole canal leaf (B);

FIG. 3A-C shows the shape of a leaf blade base (A) and leaf upper (B) and leaf lower (C) surfaces;

FIG. 4 shows typical suckers;

Figure 1:
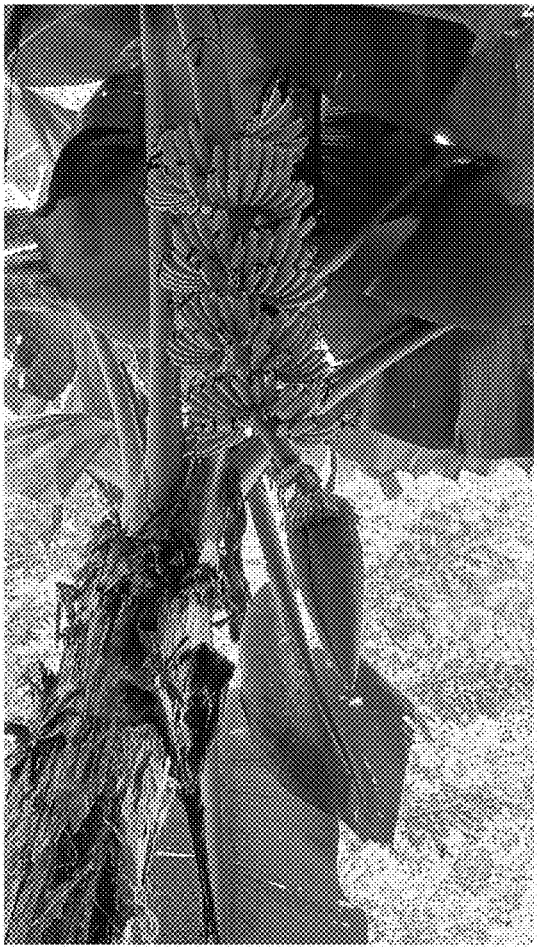
Figures 2A, 2B:
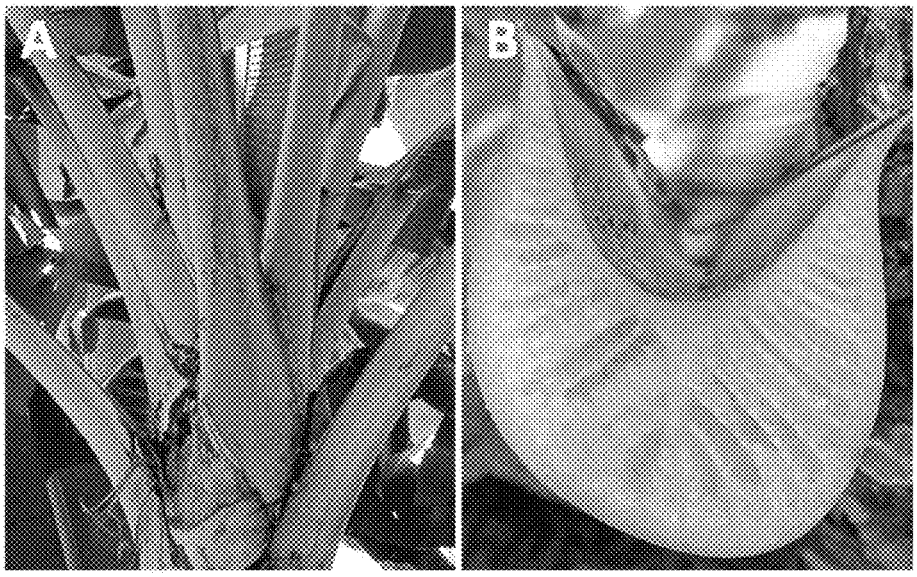
Figure 5:
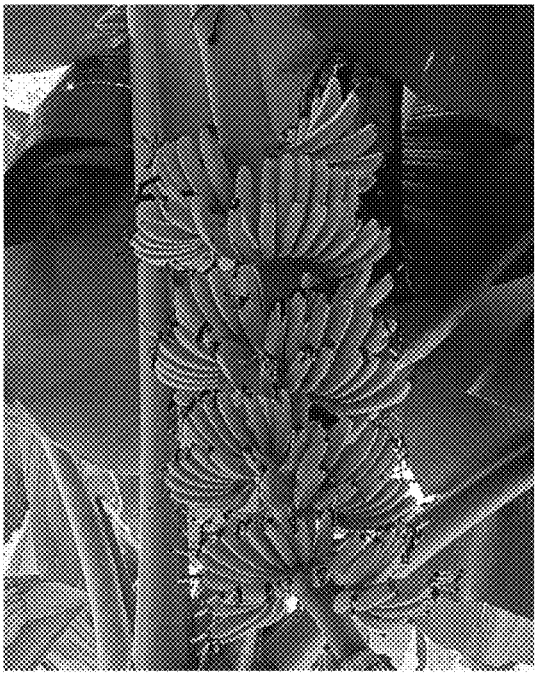
FIG. 5 shows a typical fruit bunch.
Figure 6:
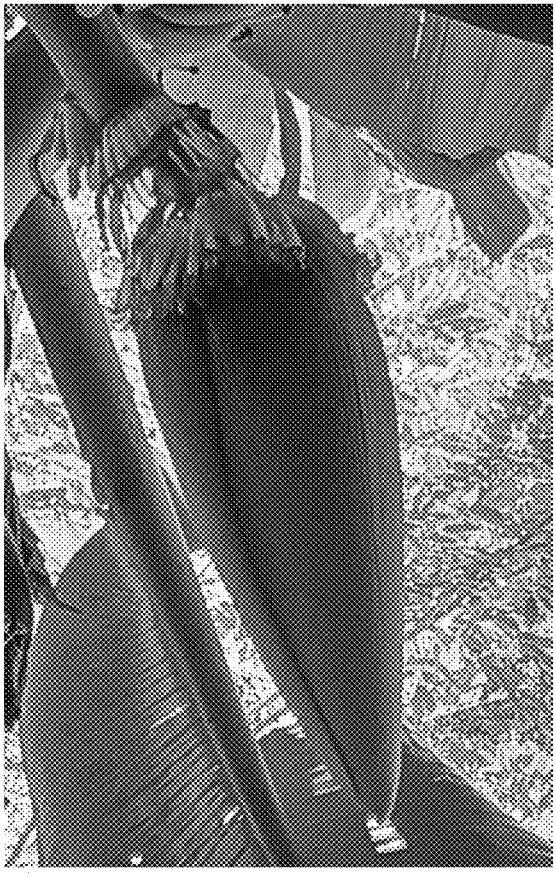
FIG. 6 shows a male bud.
Figure 8A:
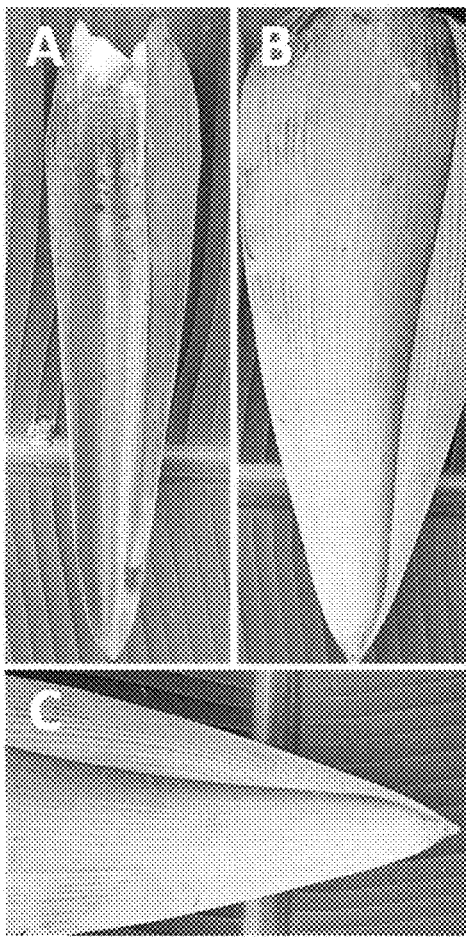
Figure 8B:
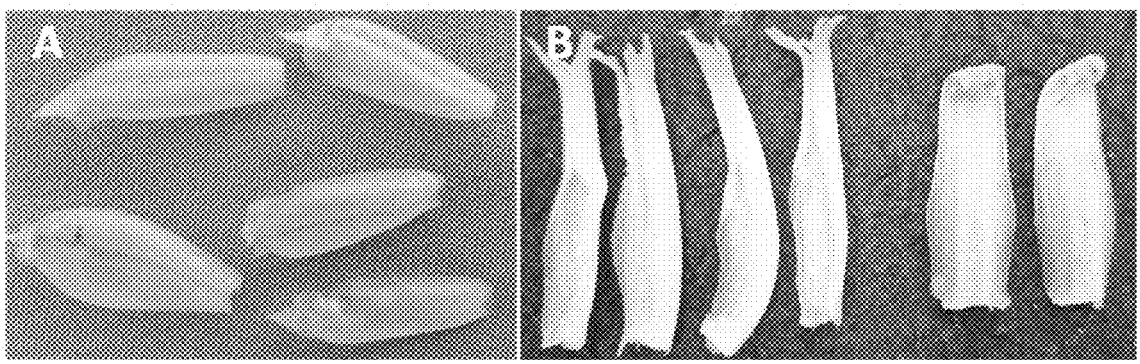
Figures 9A, 9B:
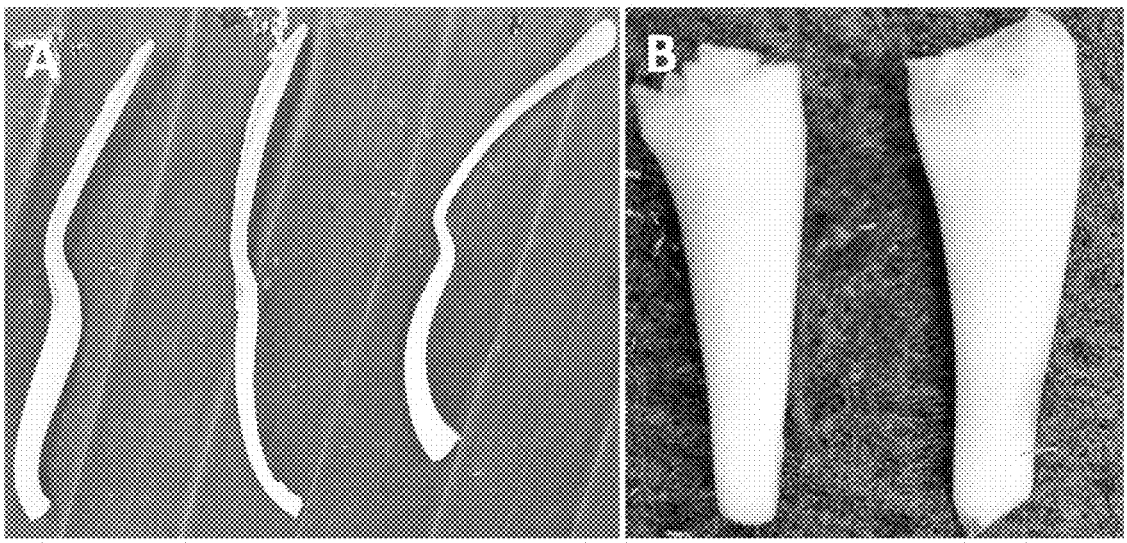
Figure 10:
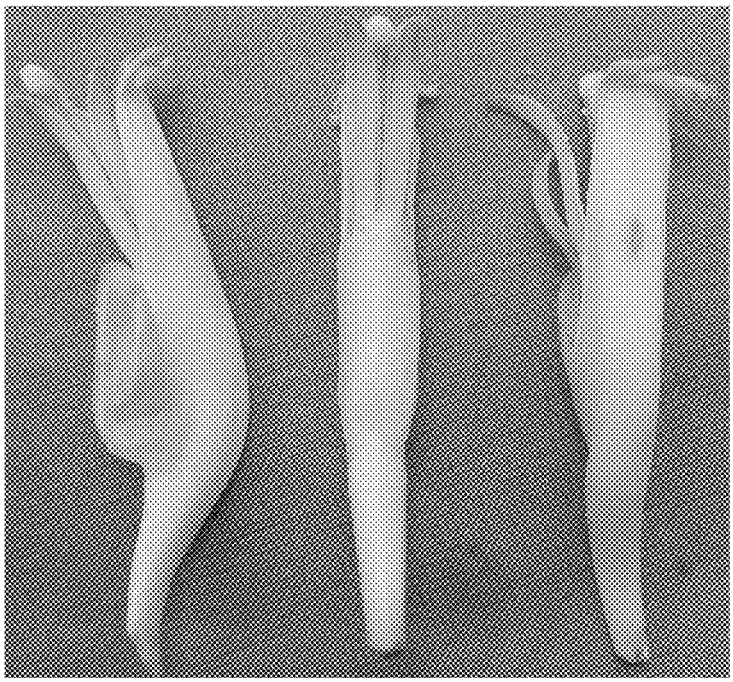
Figure 11:
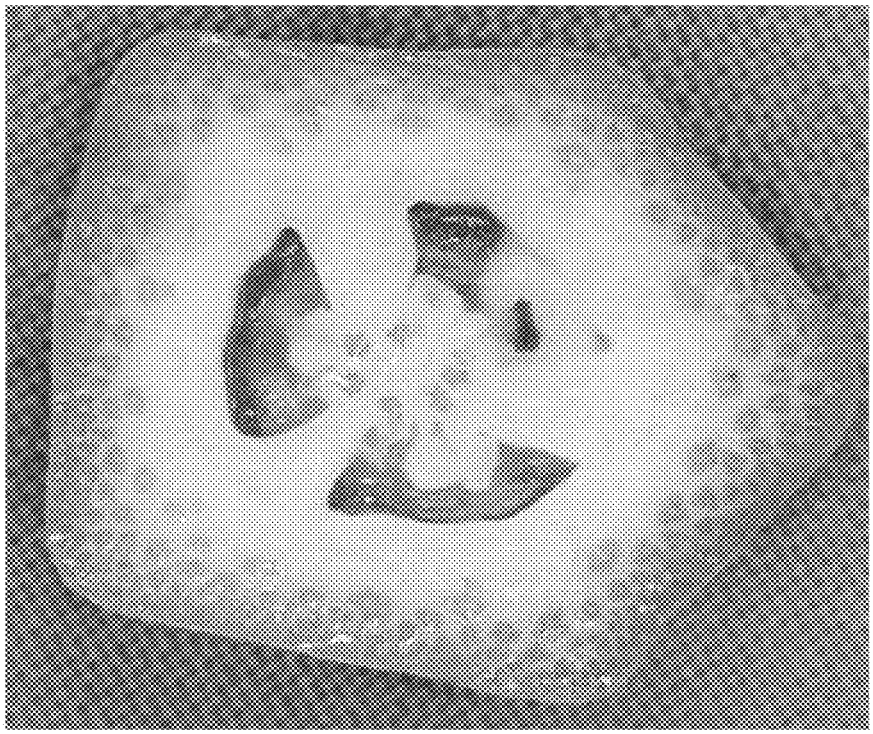

FIG. 7A-C shows bracts of a male bud;

FIG. 8A-B shows compound tepal (A) and free tepals (B) lobes;

FIG. 9A-B shows style shape (A) and ovary (B);

FIG. 10 shows a typical male flower;

FIG. 11 shows rowed ovules and

Figure 12:
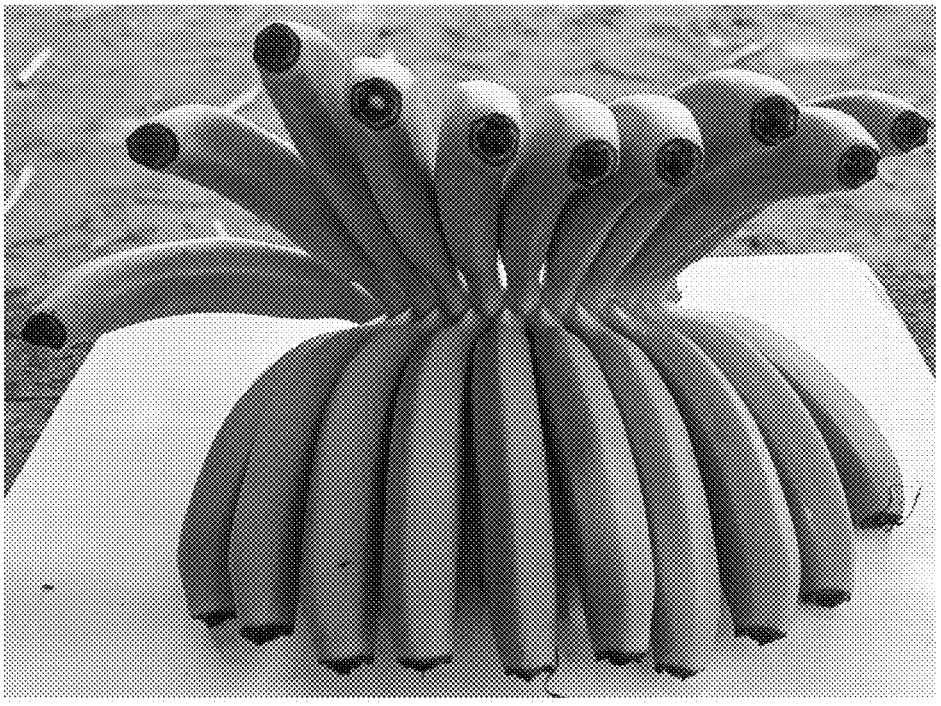

FIG. 12 shows a typical second hand.

DETAILED BOTANICAL DESCRIPTION

This report provides a thorough botanical description of the new 'WH02' variety evaluated in La Lima, Cortés, Honduras, 2023. The descriptions concord with the internationally standardized "Descriptors for Banana (*Musa* spp.)" elaborated by IPGRI/INIBAP/CIRAD, 1996 (www.inibap.org), and The U.K.'s Royal Horticultural Society's Colour Chart, 2001. The 'WH02' plant and its fruit may differ slightly from the descriptors provided due to variations in cultural practices, soil types, and climatic conditions under which the variety may be cultivated.

| | |
|---|---|
| Leaf habit | Intermediate |
| Dwarfism | tall |
| Pseudostem height | ≥3 meters |
| Pseudostem length | 2.46 m |
| Pseudostem diameter | 61 cm |
| Pseudostem aspect | Robust |
| Pseudostem color | Green (141C, RHS) |
| Pseudostem appearance | Shiny (not waxy) |
| The predominant underlying color of the pseudostem | Yellow-Green (150D, RHS) |
| Pigmentation of the underlying pseudostem | Greyed-Purple (187B, RHS) |
| Sap color | Watery (155D, RHS) |
| Wax-on leaf sheaths | Very few waxes |
| Number of suckers | 4 |
| Development of suckers | >¼ of the height of the parent plant |
| Position of suckers | Close to parent (vertical growth) |
| Blotches at the petiole base | Small blotches |
| Blotches color | Grey-Brown (N196A, RHS) |
| Petiole canal leaf III | Wide with erect margins |
| Petiole margins | Winged and clasping the pseudostem |
| Wing type | Dry |
| Petiole margin color | Without color |
| Edge of petiole margin | Colourless (Without a color line along) |
| Petiole margin width | 1 to 2 cm |
| Leaf blade length | 171 to 220 cm |
| Leaf blade width | 81 to 90 cm |
| Petiole length | 45 to 50 cm |
| Color of the leaf's upper Surface | Green (137A, RHS) |
| Appearance of leaf upper surface | Dull |
| Color of the leaf's lower surface | Green (N139B, RHS) |
| Appearance of leaf lower surface | Dull |
| Wax on leaves | Few waxes |

-continued

| | |
|---|---|
| Insertion point of leaf blade on petiole | Symmetric |
| Shape of the leaf blade base | Both sides rounded |
| Leaf corrugation | Even, smooth |
| Color of midrib dorsal surface | Green (138B, RHS) |
| Color of midrib ventral surface | Yellow-Green (145C, RHS) |
| Color of cigar leaf dorsal surface | Green (139C, RHS) |
| Blotches on leaves of water suckers | Without blotches |
| Peduncle length | 61 to 68 cm |
| Empty nodes on the peduncle | Two or more |
| Peduncle width | 7-12 cm |
| Peduncle color | Green (137B, RHS) |
| Peduncle hairiness | Very hairy, short hairs (similar to velvet touch) |
| Bunch position | Hanging vertically |
| Bunch shape | Cylindrical |
| Bunch appearance | Lax |
| Bunch length | 120 cm |
| Bunch diameter | 66 cm |
| Number of hands of the bunch | 12 |
| Flowers that form the fruit | Female |
| Fruits | Biseriate |
| Rachis type | Present and male buds may be degenerated or persistent. |
| Rachis position | With a curve |
| Rachis appearance | Bare |
| Male bud type | Normal (present) |
| Male bud shape | Like a top |
| Male bud size | 31 cm |
| Bract base shape | Large shoulder |
| Bract apex shape | Pointed |
| Bract imbrication | Old bracts overlap at the apex of the bud. |
| Color of the bract external face | Greyed-Orange (177D, RHS) |
| Color of the bract internal ace | Yellow (10D, RHS) |
| Color of the bract apex | Tinted with yellow (discolored) (7C, RHS) |
| Color stripes on the bract | Without discolored lines or stripes on the external face |
| Bract scars on rachis | Very prominent |
| Persistence of the bracts of the rachis | Moderate |
| Fading of color on bract base | Color discontinuing towards the base. |
| Male bract shape | Ovate |
| Male bract lifting | Lifting one at a time |
| Bract behavior before falling | Revolute (Rolling) |
| Wax on the bract | Moderately waxy |
| Presence of grooves on the bract | Moderate |
| Male flower behavior | Falling after the bract |
| Compound tepal basic color | White (155C, RHS) |
| Compound tepal pigmentation | Very few or no visible signs of pigmentation |
| Lobe color of compound tepal | Greyed-Orange (163B, RHS) |
| Lobe development of compound tepal | Developed |
| Free tepal color | Opaque White (155D, RHS) |
| Free tepal shape | Oval |
| Free tepal appearance | Simple folding under the apex |
| Free tepal apex development | Little or no visible sign of development |
| Free tepal apex shape | Thread-like |
| Anther exsertion | Inserted |
| Filament color | Greyed-White (156D, RHS) |
| Anther color | Green-White (157C, RHS) |
| Pollen sacs color | Greyed-Red (198D, RHS) |
| Pollen vitality | Medium |
| Style basic color | Green-White (157C, RHS) |
| Pigmentation on style | Without pigmentation |
| Style exsertion | Inserted |
| Style shape | Curved at the base |
| Stigma color | Yellow-Orange (14A, RHS) |
| Ovary shape | Arched |
| Ovary basic color | Green (142D, RHS) |

-continued

| | |
|---|---|
| Ovary pigmentation | Very few or no visible signs of pigmentation |
| Dominant color of male flower | White 155C, RHS) |
| Irregular flowers | Absent |
| Arrangement of ovules | Two rowed |
| Fruit position | Parallel to the stalk |
| Number of fruits | 17 to 20 |
| Fruit length | 13 to 15 cm |
| Fruit width | 3.2 cm |
| Fruit shape (longitudinal curvature) | Curved (sharp curve) |
| Color of the flesh of the fruit | Creamy (158C, RHS) |
| Longitudinal ridges of the fruit | Moderate |
| Transverse section of fruit | Slightly ridged |
| Fruit apex | Blunt-tipped |
| Remains of flower relicts at the fruit apex | Persistent style |
| Fruit pedicel length | 21 to 23 mm |
| Fruit pedicel width | 5 to 10 mm |
| Pedicel surface | Hairy |

-continued

| | |
|---|---|
| Fusion of pedicel | Very partially or no visible sign of fusion |
| Immature fruit peel color | Green (141D, RHS) |
| Mature fruit peel color | Yellow-Orange (14C, RHS) |
| Fruit peel thickness | 2 to 3 mm |
| Adherence to the fruit peel | Fruit peels easily |
| Cracks in fruit peel | Cracked |
| Pulp in fruit | With pulp |
| Pulp color before maturity | White (N155D, RHS) |
| Pulp color at maturity | Yellow-Orange (18B, RHS) |
| Fruits fall from hands. | Deciduous |
| Flesh texture | Firm |
| Predominant taste | Sweet (like Cavendish) |
| Presence of seed with the source of pollen | Without seeds |
| Seed surface | Without seeds |
| Seed shape | Without seeds |
| Growth habit of the plant | Upright |

The invention claimed is:

1. A new and distinct variety of banana plant named 'WH02', substantially as illustrated and described herein.

* * * * *

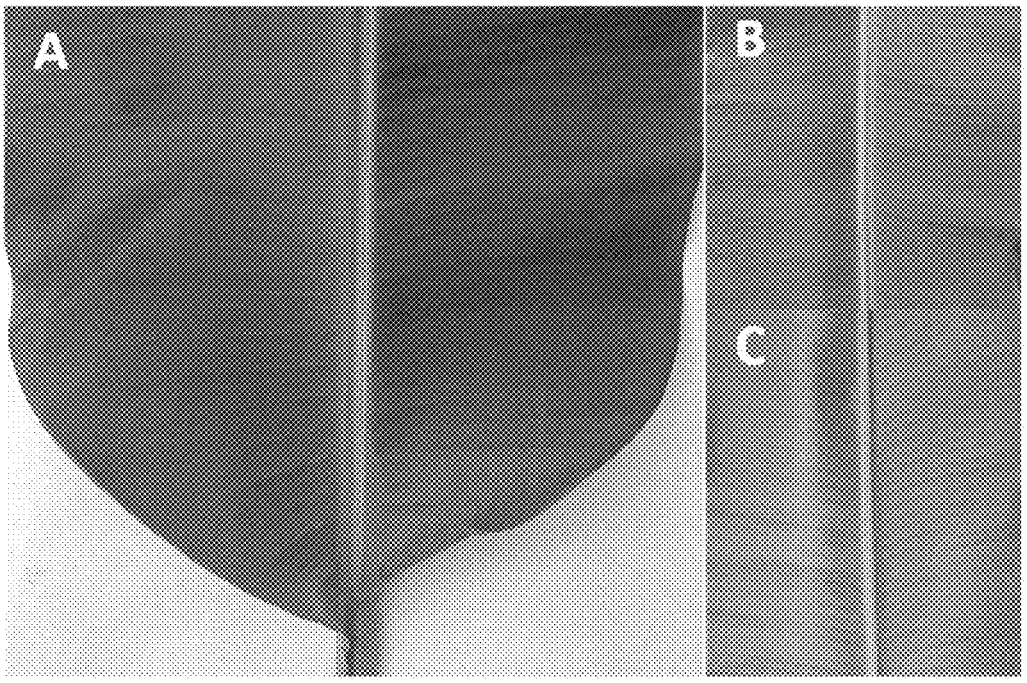
FIG. 3A, 3B, & 3C
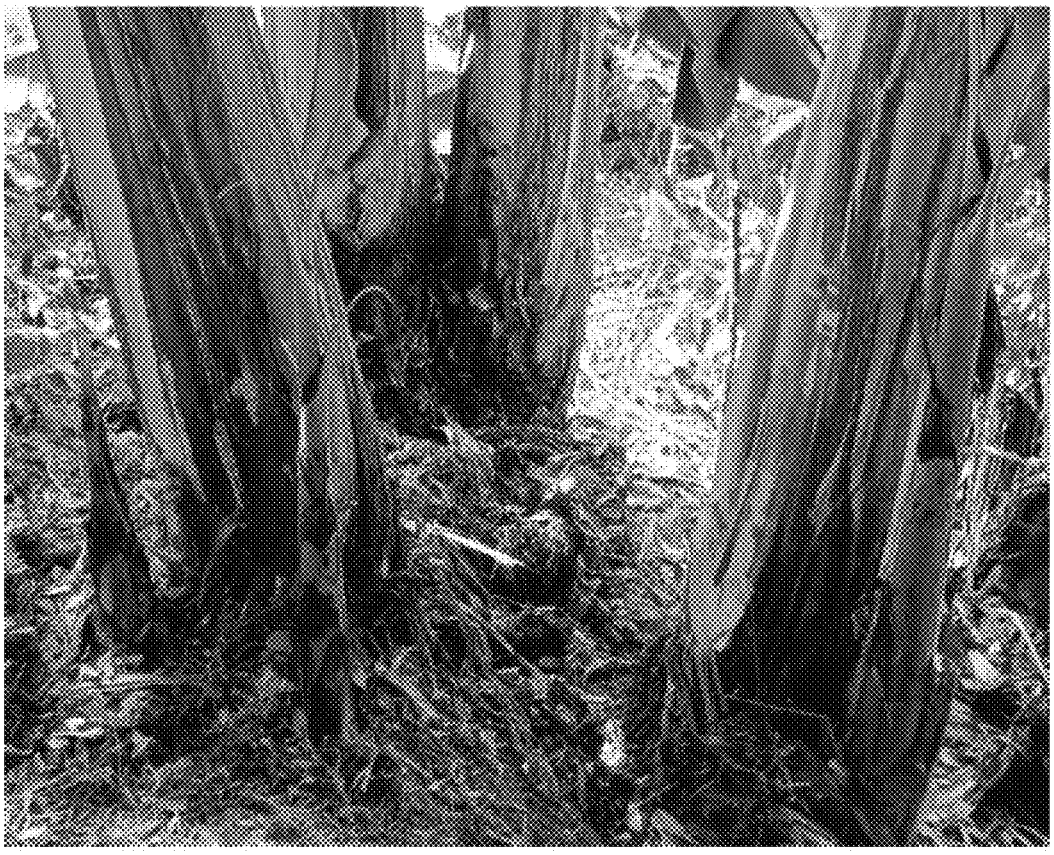
FIG. 4

FIG. 7A, 7B, & 7C